United States Patent [19]

Tenney, Jr.

[11] 4,408,597
[45] Oct. 11, 1983

[54] PROSTHETIC OCCLUSIVE DEVICE FOR AN INTERNAL PASSAGEWAY

[75] Inventor: John B. Tenney, Jr., Williamson, N.Y.

[73] Assignee: The United States of America as represented by the Administrator of the National Aeronautics and Space Administration, Washington, D.C.

[21] Appl. No.: 371,352

[22] Filed: Apr. 23, 1982

[51] Int. Cl.³ .................................... A61B 19/00
[52] U.S. Cl. ............................ 128/1 R; 128/346; 128/DIG. 25
[58] Field of Search ............... 128/1 R, DIG. 25, 325, 128/344, 346, 686, 24 R, 327, DIG. 20; 604/101

[56] References Cited
U.S. PATENT DOCUMENTS

| | | | |
|---|---|---|---|
| 3,580,248 | 5/1971 | Larson | 128/DIG. 20 |
| 4,019,499 | 4/1977 | Fitzgerald | 128/1 R |
| 4,222,377 | 9/1980 | Burton | 128/1 R |
| 4,256,093 | 3/1981 | Helms et al. | 128/DIG. 25 |

Primary Examiner—Lee S. Cohen
Assistant Examiner—Christine A. Fukushima
Attorney, Agent, or Firm—Joseph H. Beumer; John R. Manning; Leon D. Wofford, Jr.

[57] ABSTRACT

An occlusive device is disclosed for surgical implant to occlude the lumen of an internal organ. The device includes a cuff A having a backing collar (10) and two isolated cuff chambers B and C. The fluid pressure of chamber B is regulated by a pump/valve reservoir unit E. Chamber C is unregulated in pressure but its fluid volume is adjusted by removing or adding fluid to a septum/reservoir D by means of a hypodermic needle. Pressure changes are transmitted between the two cuff chambers via faying surfaces (12) and (14) which are sufficiently large in contact area and thin as to transmit pressure generally without attenuation. By adjusting the fluid volume of septum D, the operating pressure of the device may be adjusted to accommodate tubular organs of different diameter sizes as well as to compensate for changes in the organ following implant without re-operation.

6 Claims, 10 Drawing Figures

PROSTHETIC OCCLUSIVE DEVICE FOR AN INTERNAL PASSAGEWAY

ORIGIN OF THE INVENTION

The invention described herein was made in performance of work under a NASA Contract, and is subject to the provisions of Section 305 of the National Aeronautics and Space Act of 1968, Public Law 85-568 (72 Stat. 435.002 U.S.C. 2457).

BACKGROUND OF THE INVENTION

The invention relates to a prosthetic occlusive device for occluding an internal passageway of the human body, for example, for closing the urinary canal in controlling the bladder function where a person has lost bladder control. Implantable devices have been used before for controlling bladder functions and for occluding other internal passageways in the human body such as shown in U.S. Pat. Nos. 2,455,289; 3,750,194; and 3,863,622; which utilize an inflatable or pressurized cuff which is pressurized by means of a fluid actuator. U.S. Pat. No. 4,019,499 discloses an implant device for urinary incontinence in which the fluid volume and pressure may be adjusted after implant. However, devices of these types do not effectively accommodate tubular organs of varying diameters nor effectively permit readjustment of operating pressures due to changing conditions after implant.

In the cuff type devices, fluid cannot be readily added intra-operatively due to the inherent characteristics of the designs of the prior art devices and fluid cannot be added postoperatively without re-operation. Accordingly, no adjustment can be made to the device for growth, atrophy or scarring by means of adding or removing fluid after implantation.

Furthermore, it has been found that the prior art devices have not been entirely satisfactory in control of the pressures required to effectively occlude the organ. The pressurization actually transmitted to cuff and organ may exceed or be less than that required to occlude the organ due to changed conditions. Excess pressures to the organ often results in tissue damage to the organ.

Accordingly, an important object of the present invention is to provide an occlusive device for occluding a tubular organ in which operating pressure adjustments may be made in an implanted device to compensate for changing patient conditions such as growth, atrophy, and scarring without separating.

Yet another important object of the present invention is to provide an occlusive device for occluding tubular organs which will readily accommodate organs of different diameters.

Still another important object of the present invention is to provide an occlusive cuff device for occluding an organ in which fluid may be added to or removed from the device after implantation for adjusting operating pressures.

Yet another important object of the present invention is to provide an occlusive device for surgical implantation for occluding a tubular organ wherein the fluid volume required to effect closure may be sent within a limited range by utilizing a two-chamber inflatable cuff wherein one chamber is attached to a pressurizing valve, and the other chamber is attached to a subcutaneously implanted septum in which fluid can be added subcutaneously by means of a hypodermic needle.

SUMMARY OF THE INVENTION

The above objectives are accomplished according to the present invention by means of an inflatable cuff having an outer collar which may be fitted around a tubular organ and which includes two separate isolated pressurization chambers. These chambers are designed so that in a static configuration they are in contact over a faying surface having an area which is roughly equivalent to the diameter of the cuff collar. In this configuration, the individual chambers are expanded but unstressed. The cuff collar is reinforced to make it more resistant to deformation than the inner faying surfaces of the chambers. When fluid is added to either chamber, the internal pressure is increased and by making the walls of the chambers sufficiently thin, pressure is transmitted across the faying surfaces with minimal attenuation. In other words, a pressure increase in one chamber would increase the pressure in the other chamber to approximately the same level.

The tubular organ is fitted between the faying surfaces and opened and closed by pressurization thereof accordingly. One of the chambers is connected to a pressurizing pump/valve for regulating and actuating the device and the other chamber is unregulated but connected to a septum which is implanted with the device. By adjusting the fluid volume and pressure in the unregulated chamber, the single size cuff device chambers, the single size cuff device may be adapted to occlude organs of varying diameters and sizes. This eliminates or minimizes having a wide range of cuff sizes. This also permits adjustment for when the organ changes in diameter as occurs through scarring, growth and aging without requiring cuff replacement and re-operation.

BRIEF DESCRIPTION OF THE DRAWINGS

The construction designed to carry out the invention will be hereinafter described, together with other features thereof.

The invention will be more readily understood from a reading of the following specification and by reference to the accompanying drawings forming a part thereof, wherein an example of the invention is shown and wherein.

DESCRIPTION OF A PREFERRED EMBODIMENT

Figure 1:
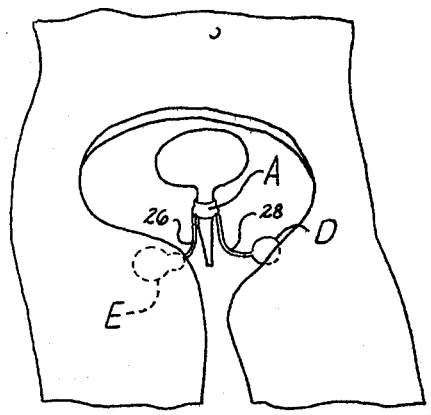
FIG. 1 is a partially cut-away view illustrating an occlusive device surgically implanted for occluding a tubular organ.
Figure 2:
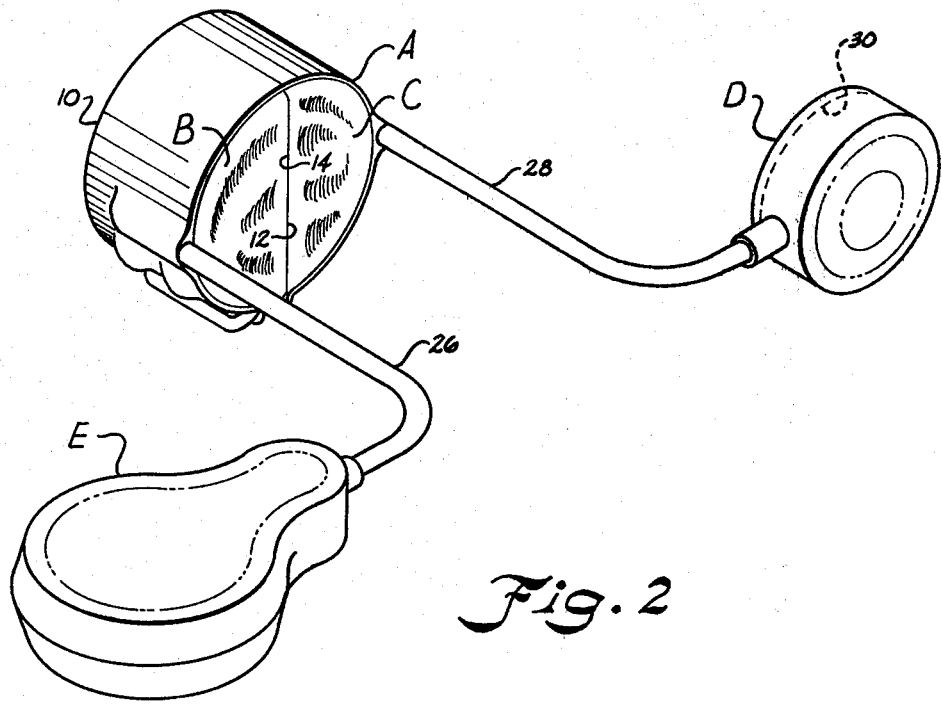
FIG. 2 is a perspective view illustrating an occlusive system for occluding a tubular organ constructed according to the invention.

The invention is directed to an occlusive device which includes an inflatable cuff means A which can be opened or closed after surgical implantation for purposes of occluding the lumen of a tubular organ such as the colon, ileum, urethra, ureters, etc. While the device may be applied to any tubular organ, the invention is shown as applied to an urethra for purposes of illustration.

To be successful, a hydraulically actuated occlusive cuff must act within a range of pressures which are determined by the body. At the high end, the cuff pressure must be high enough to occlude the lumen of the organ without shutting off blood supply and causing tissue damage. When this pressure is known, a suitable regulator valve, such as shown in U.S. Pat. No. 4,256,093, can be employed to insure that the closing pressure is not exceeded when the cuff is pressurized and that the pressure level drops only as is needed to permit the fluid to again move through the previously occluded lumen. If the cuff is adjusted to the tubular organ intraoperatively, the desired pressure change can occur with only a small change of fluid volume. This permits the volume of fluid required in the valve reservoir to be small. This is a desirable attribute since the fluid reservoir is also part of the implanted device and occupies space in the body. Ideally, the smallest sizes consistent with successful function are preferred for all elements of such systems.

Referring now in more detail to the drawings, an occlusive cuff device A is illustrated for surgical implantation in the human body which includes a cuff collar means 10 and a first cuff pressure chamber B and a second, isolated cuff pressure chamber C. Cuff chamber B is regulated and pressurizable for effecting closure of the lumen of the organ. Cuff chamber C is unregulated during operation. Each pressure chamber includes a faying surface 12 and 14, between which surfaces the organ is fitted. A subcutaneous septum means D is connected in fluid communication with the chamber C so that the fluid volume of the septum and hence chamber C may be adjusted accordingly post or intraoperatively.

The walls of the inflatable chambers B and C are thin and flexible and the thickness is determined by consideration of pressures, shape and materials. In general, the thin walls are sufficiently compliant to permit the conformance of the cuff chamber with the geometry of the tubular organ which is being occluded. Faying surfaces 12 and 14 of the chambers B and C, respectively, must be in contact over a substantial area which is preferably equivalent to the area defined by the diameter of the cuff collar 10 and its width. When both chambers B and C are filled with a suitable fluid, typically saline with an appropriate radioopaque tag material, and when both chambers are extended to their full unstressed limits at a low internal pressure, the volume change to either chamber should create a pressure change in that chamber which is transmitted with very little diminution to the opposite side. The large faying surfaces provide minimal attenuation of the pressure transmitted thereto from pressure chamber B to chamber C for effective occlusion. This eliminates cusps and other discontinuities associated with other conventional cuff shapes.

The two independent and isolated cuff chambers B and C may be connected to suitable valves, fluid reservoirs, regulating reservoirs, septa or other system elements. In a preferred embodiment, cuff chamber B is connected to a pressure regulator valve E which prevents internal pressure levels from exceeding desired operational levels, and chamber C is connected to a subcutaneous septum/reservoir D. A suitable valve for use as the pressure regulation value E is disclosed in U.S. Pat. No. 4,256,093. If excess fluid pressure is transmitted into the cuff chamber B the valve will crack and let fluid bleed back into the reservoir forming a part thereof. If internal pressure in the unregulated chamber C were inadvertently increased above design levels this increase would be transmitted to the faying surface and to the opposite cuff chamber B again causing the valve to crack and bleed back into the reservoir.

The cuff collar 10 is preferably a deformation resistant backing the outer contour of which is reinforced to restrict outward radial deformation and to force fluid pressure to deform the thin wall cuff chambers in the direction of their faying surfaces in the organ which is being occluded. The cuff collar 10 includes split ends 16 and 18 which accommodate placement of the cuff collar and cuff chambers about the organ. Latch means for securing the free ends of the cuff collar together is illustrated in the form of a latch eye 22 and a latching member 24 which may be inserted in the eye 22 and hooked therein. The cuff collar 10 and latching means are integral such as they present a smooth contour surface which is compatible with either encapsulation or ingrowth. The latching member 24 and eye 22 hold the ends of the cuff together and prevent separation when pressure is applied for occluding the tubular organ. All cuff materials including the illustrated latch are preferably formed or molded from suitable biocompatible material such as a medical grade silicon rubber.

Valve/reservoir E is connected in fluid communication to regulated chamber B by tubing 26.

Septum/reservoir means D is connected to the cuff chamber C by means of tubing 28 placing the two together in fluid communication so that fluid volume of the cuff chamber C may be adjusted by adjusting the volume of fluid in the septum by means of a hypodermic needle. For this reason, septum means D is implanted subcutaneously for reliable needle access. The septum permits the introduction of fluid intra-operatively without the penetration or contamination of the previously sealed valve side. In this way, the static pressure of the cuff/chamber C, that is with the tubular organ still open, can be raised to a desired level at which a small desired increase will effectively occlude the organ. The subcutaneous placement of the septum provides for postoperative adjustment of cuff pressure without surgery due to changes in the size of the organ which may be caused by changes in weight, age, scarring, disease, or a device malfunction. The septum is preferably provided with a needle stop 30 to prevent the needle from penetrating the septum.

Figure 3:
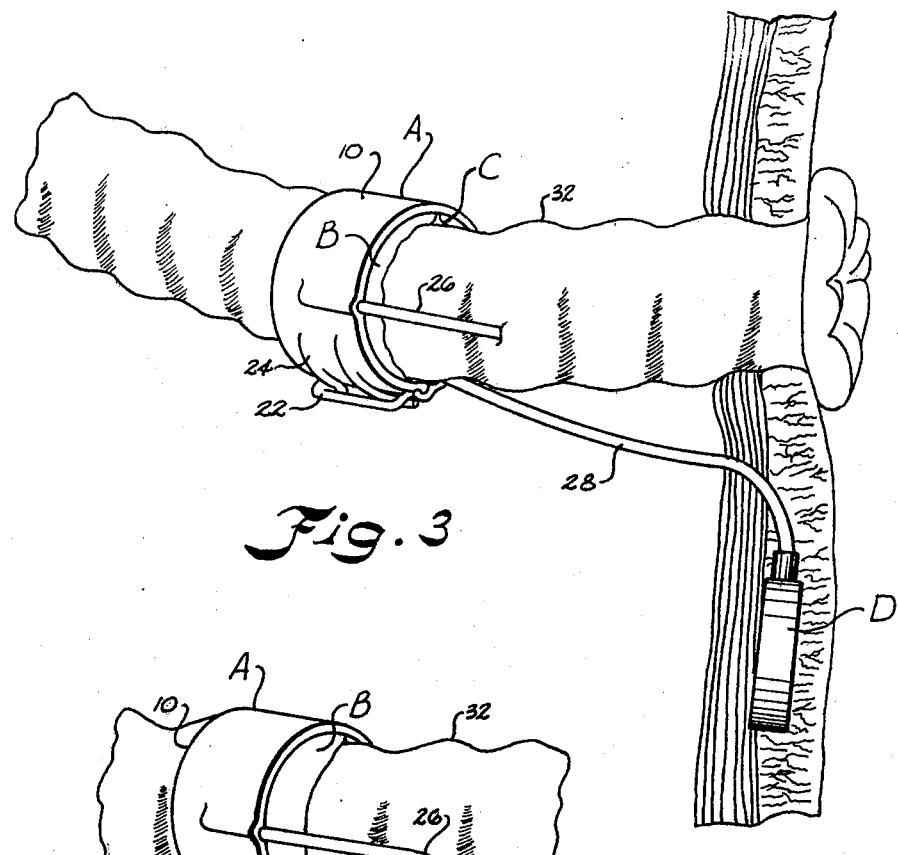
FIG. 3 is an enlarged view illustrating an occlusive device constructed according to the present invention as fitted about the colon with the device in a static state.
Figure 3A:
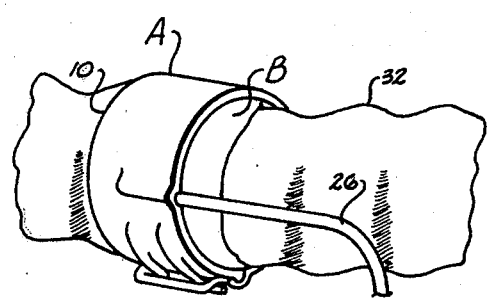
FIG. 3A is a perspective view illustrating the device of FIG. 3 in a pressurized state for occluding the lumen of the colon.

FIGS. 3a and 3 illustrate application of the device to the lumen of urethra 32 with the cuff means A in a static state in FIG. 3 wherein the lumen is opened and a pressurized state in FIG. 3a in which regulated chamber B is pressurized for occluding the lumen.

The cuff chamber C and septum D may be utilized to adapt the occluding device to a range of organ diameters and sizes by adjusting the fluid volume in the unregulated chamber C of cuff means A. This can best be seen in FIGS. 4a, b, c and 5a, b, c,.

Figures 4A, 4B, 4C:
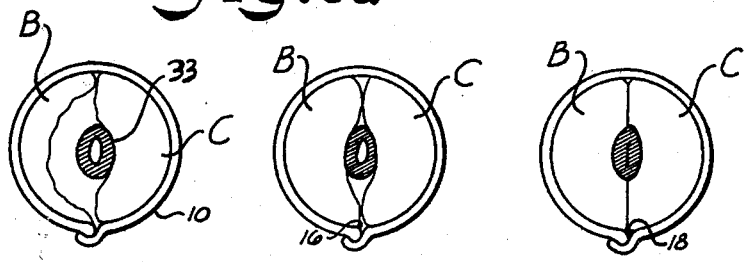
FIGS. 4A–4C are a series of schematic views illustrating an occluding device constructed according to the present invention fitted about a small urethra.

In FIGS. 4a–c adaptation of the occlusive cuff device is illustrated with a small urethra 33. In step a, cuff means A is illustrated with the cuff chamber C in its normally fluid filled condition surrounding the urethra and cuff chamber B unfilled with fluid. In step b, cuff chamber B is filled to a fluid volume and pressure at which the lumen of the urethra remains open and in which the device is essentially static. In step c, the device is illustrated with the cuff chamber B pressurized by means of the pump valve E such that the regulated pressure transmits a change in pressure through the faying surfaces 12 and 14 to the organ which is sufficient to effect closure of the lumen.

Figures 5A, 5B, 5C:
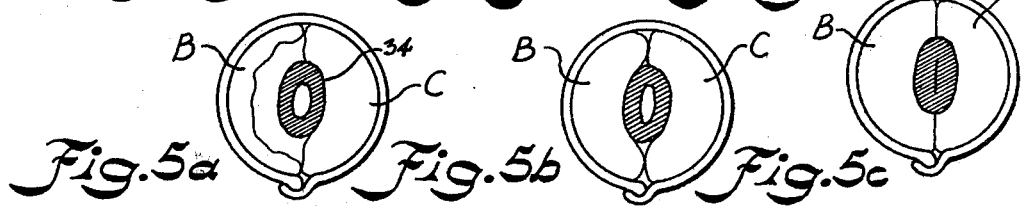
FIGS. 5a–5c are a series of schematic views illustrating an occlusive device of FIGS. 4a–4c adapted to a large urethra.

In FIGS. 5a-c, the cuff is shown fitted around a larger urethra 34 wherein the same steps are followed but this time a smaller fluid volume would be needed in the cuff chamber C which could be adjusted by removing fluid or adding less fluid to the septum D. With the volume and pressure of chamber C adjusted, the larger urethra remains open in step b with the same fluid volume in chamber B. The cuff is still effective to effect closure of the lumen of the larger urethra by actuation of pump valve E.

Thus, it can be seen that a highly advantageous construction can be had for an occlusive device according to the invention which may be easily adapted to tubular organs of different size diameters and in which the operational condition of the device may be adjusted to compensate for changes in the condition of the tubular organ as often occurs through aging, atrophy, or scarring. The occlusive cuff device may be adjusted to the tubular organ intra-operatively by removing or adding fluid to provide just the right pressure conditions such that the pressures transmitted by the pump valve E do not exceed that required for occluding the lumen as may lead to the closing off of the blood supply and accompanying tissue.

While a preferred embodiment of the invention has been described using specific terms, such description is for illustrative purposes only, and it is to be understood that changes and variations may be made without departing from the spirit or scope of the following claims.

What is claimed is:

1. An occlusive cuff device for surgical implantation in the human body for the purpose of opening and closing an internal passageway in a tubular organ and the like comprising:
   cuff means including a first and second isolated cuff pressure chamber;
   said first cuff chamber being regulated and pressurizable for effectively occluding said passageway of said tubular organ;
   said second cuff chamber being unregulated during normal operation of said device;
   each said cuff chamber including a faying surface in which said passageway is receivably fitted;
   a deformation resistant cuff collar encircling said two cuff chambers; and
   a fluid containing septum means in fluid communication with said second cuff chamber adapted for subcutaneous placement so that the fluid volume of said septum means and hence said second chamber may be adjusted accordingly by means penetrating the skin to accommodate use on organs of different diameter sizes and to compensate for changing organ conditions without re-operation.

2. The device of claim 1 wherein said collar is split having free ends accommodating placement thereof over said organ and including latch means for securing said ends of said cuff collar together.

3. The device of claim 1 including pump/valve means connected to said first cuff chamber for selectively regulating and pressurizing said first cuff chamber for occluding said passageway.

4. The device of claim 1 wherein said first and second cuff chambers comprise thin wall flexible material.

5. The device of claim 1 wherein said faying surfaces are of sufficient dimension and contact with one another as to cause the pressure changes to be transmitted across said faying surfaces from either cuff chamber without significant attenuation of said pressure.

6. The device of claim 1 wherein said faying surfaces are in contact over an area generally equivalent to the area defined by the diameter of said cuff collar and its width.

* * * * *